United States Patent [19]
Blessing et al.

[11] Patent Number: 4,738,139
[45] Date of Patent: Apr. 19, 1988

[54] ULTRASONIC REAL-TIME MONITORING DEVICE FOR PART SURFACE TOPOGRAPHY AND TOOL CONDITION IN SITU

[76] Inventors: Gerald V. Blessing, 5017 Camelback Lane, Frederick, Md. 21701; Donald G. Eitzen, 11516 Alcinda La., Gaithersburg, Md. 20878

[21] Appl. No.: 1,905
[22] Filed: Jan. 9, 1987
[51] Int. Cl.⁴ .............................................. G01N 29/00
[52] U.S. Cl. ......................................... 73/644; 73/105
[58] Field of Search ................. 73/644, 105, 627, 642, 73/629

[56] References Cited
U.S. PATENT DOCUMENTS 3,534,590 10/1970 Kent et al. ............................ 73/618
3,688,569 9/1972 Murdoch .............................. 73/105
4,364,264 12/1982 ReFiorentin .
4,403,510 9/1983 deWalle et al. .
4,507,969 4/1985 Djordjevic et al. .

Primary Examiner—Jerry W. Myracle
Attorney, Agent, or Firm—Schwartz, Jeffery, Schwaab, Mack, Blumenthal & Evans

[57] ABSTRACT

An ultrasound device sends and guides ultrasonic waves to a part surface through a fluid in laminar flow along a curved path, and then receives the reflected and/or scattered waves from that surface in the mode of a sensor. The received signal yields information about the part surface topography such as roughness, scratches, and dents. Since the device can operate in real-time in situ on moving, as well as on stationary parts, the received ultrasonic signal may be used to monitor tool wear during part fabrication, and even provide feedback information for machine control.

30 Claims, 4 Drawing Sheets

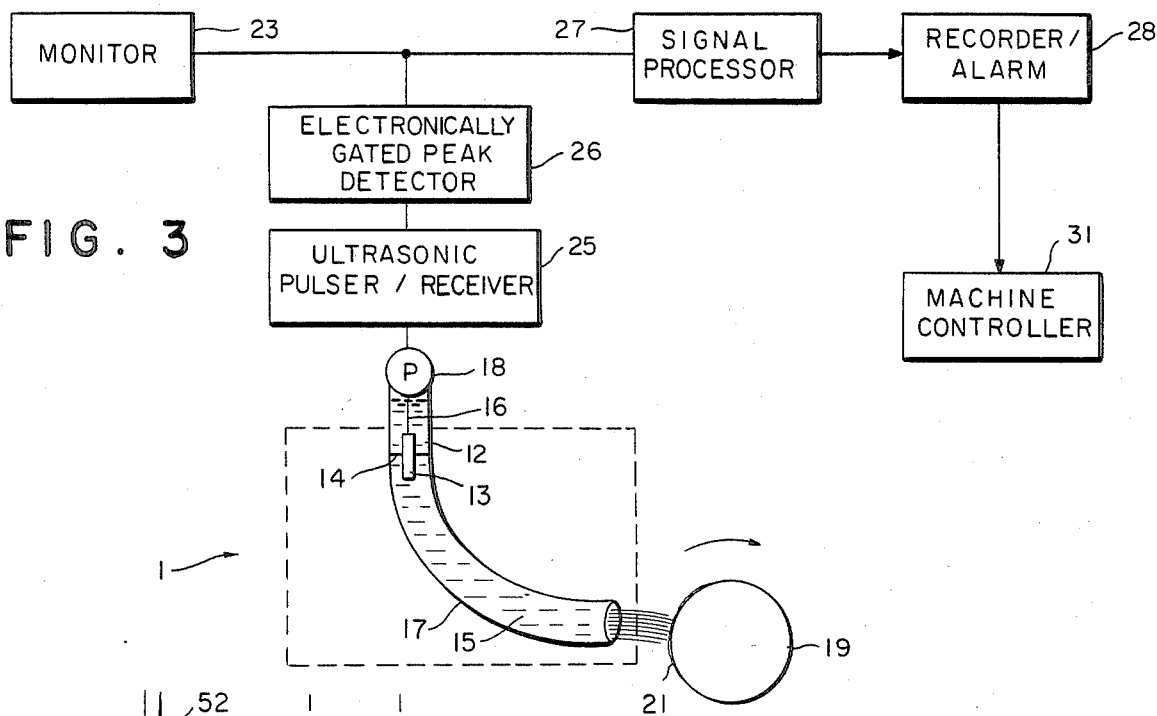
FIG. 3
FIG. 4
FIG. 5
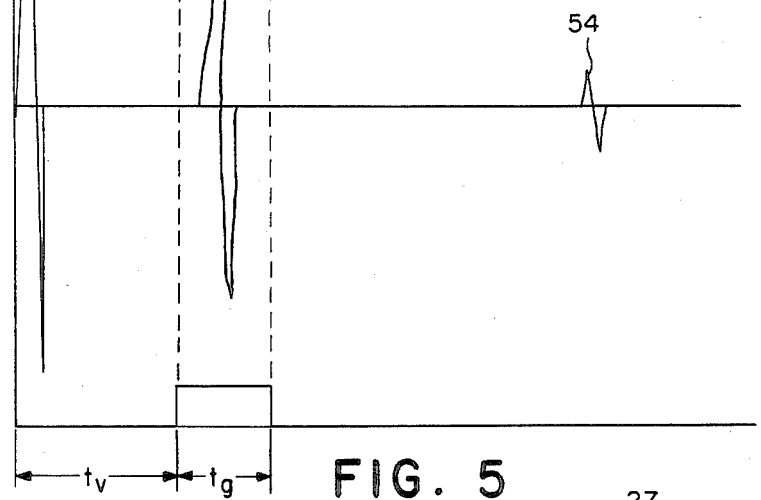
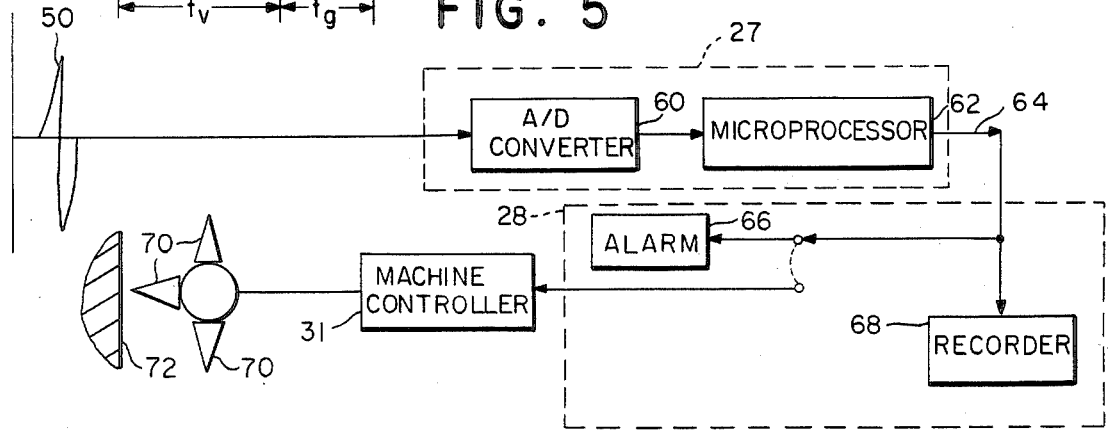

ULTRASONIC REAL-TIME MONITORING DEVICE FOR PART SURFACE TOPOGRAPHY AND TOOL CONDITION IN SITU

INTEREST OF U.S. GOVERNMENT

The U.S. Government has a non-exclusive, royalty-free license in and to the invention described and claimed herein.

BACKGROUND OF THE INVENTION

The invention relates to an ultrasonic monitoring device, and in particular to a real-time ultrasonic device for monitoring machine part surface topography and tool condition in situ.

The invention applies to a large range of surface topographies from the microscopic, where the surface feature dimensions are very small and typically expressed in microinches, to the macroscopic where the surface features are much larger. A descriptor often associated with a microscopic topography is "average surface roughness" (or simply "surface roughness") because the measuring probe typically averages over a region much larger than the region of an individual feature such as a surface peak or valley. Measuring the detailed shape of individual features, whether it be microscopic or macroscopic in scale, may be referred to as surface profiling.

Traditionally, the machine tool operator may evaluate the surface roughness of the machined part by tactile sensing and visual observation of the stationary part and perhaps assign some quantitative measure by comparing his sense touch to that of a set of roughness artifact standards thereby indicating the condition of the tool. A stylus gauge may be used to provide a more precise roughness measure by traversing in direct contact a section of the stationary part which yields an average value of the surface topography over that section.

More recently, ultrasonic techniques have been used to determine surface roughness of parts. The basic concept of the ultrasonic technique is that the back scattered energy from an impinging ultrasonic wave is a sensitive function of the surface roughness. Examples of such prior art monitoring techniques may be found in U.S. Pat. Nos. 4,364,264 issued to Fiorentin and 3,688,569 issued to Murdoch, both of which are incorporated herein by reference.

Fiorentin measures surface roughness of a part based upon a phase measurement. A measurement probe, in contact with a surface to be measured, transmits an ultrasonic pulse to the surface and receives a reflection of the transmitted pulse from the surface. The phase difference of the reflection is indicative of the surface roughness of the part. However, the device is useful only when the probe comes in contact with the surface of the part.

Murdoch measures surface roughness by immersing the part in a liquid couplant, transmiting ultrasonic energy to the surface of the part in the couplant and measuring the amount of ultrasonic energy reflected from the surface in order to provide an indication of surface roughness. However, this procedure is limited to stationary parts and has no utility in the area of monitoring surface finish or tool conditions in-situ.

Applications of ultrasound measurement techniques further extend to the inspection of part dimensions, such as thickness. An example of such a prior art inspection technique may be found in U.S. Pat. No. 4,403,510 issued to de Walle et al incorporated herein by reference. Further, the prior art provides nozzle structure teachings such as shown in Djordjevic et al, U.S. Pat. No. 4,507,969, for the sending of fluid and ultrasonic waves through the fluid in laminar flow to the part in order to create an echo within the part. However, the echo amplitude from the interior of the part indicates only interior inhomogeneities and not surface roughness. Furthermore, the prior art is limited in that it is effective only when the laminar flow carrying the ultrasonic wave flows in a nearly straight line from the ultrasonic sending device to the part. Once the fluid is no longer disposed in a straight-line flow, the ultrasonic wave becomes distorted.

Additionally, since the nozzle must be close to the surface of the part in order to achieve a straight-line flow, the prior art is not always effective in an on-line approach to monitoring surface topography or dimensional characteristics at various locations on a machined part. Given the speed of rotation (for example, surface speeds on the order of 1000 ft/min) of a part as it is being machined, it is difficult and usually impossible to place the prior art measurement probes or nozzles close to the surface of the part. The advantage of an on-line approach is not only the real-time evaluation of surface condition, but also the capability to provide sensor feedback for machine control, and a means to evaluate tool condition in terms of its performance on the part. This requires information about surface roughness in areas on a machined part not currently capable of measurement using prior art devices.

Thus, it is an object of the present invention to provide an ultrasonic system capable of real-time recording of surface topography of a machined part in an on-line situation.

Another object of the present invention is to provide a system capable of monitoring part surface topography in order to determine tool condition in situ.

A further object of the present invention is to provide a device capable of employing the ultrasonic technique of transmitting ultrasonic waves through a fluid in laminar flow when the laminar flow cannot travel in a straight line.

Other objects and advantages of the present invention will be readily apparent from the following description and drawings which illustrate a preferred embodiment of the present invention.

SUMMARY OF THE INVENTION

An ultrasonic transducer located in a nozzle, or directly in a tubing, sends pulses of ultrasound through a fluid in laminar flow along a curved path as dictated by the tubing. The laminar flow fluid stream is directed to the surface of the part being machined. Some of the sound reflects from the surface back up through the fluid in laminar flow where it is detected by the transducer. The proportion of ultrasound reflected back is a measure of surface roughness of the part as well as tool condition in situ. In addition, the invention provides improved techniques for determining part properties such as thickness.

BRIEF DESCRIPTION OF THE DRAWING

FIG. 3 is a schematic drawing of a third embodiment according to the present invention.

FIG. 4 is a graphical representation of the front and back surface echo signals generated by the operation of the present invention.

FIG. 5 is a schematic drawing of the signal processor and recorder/alarm shown in FIGS. 1-3.

DETAILED DESCRIPTION OF THE PREFERRED EMBODIMENTS

Figure 1:
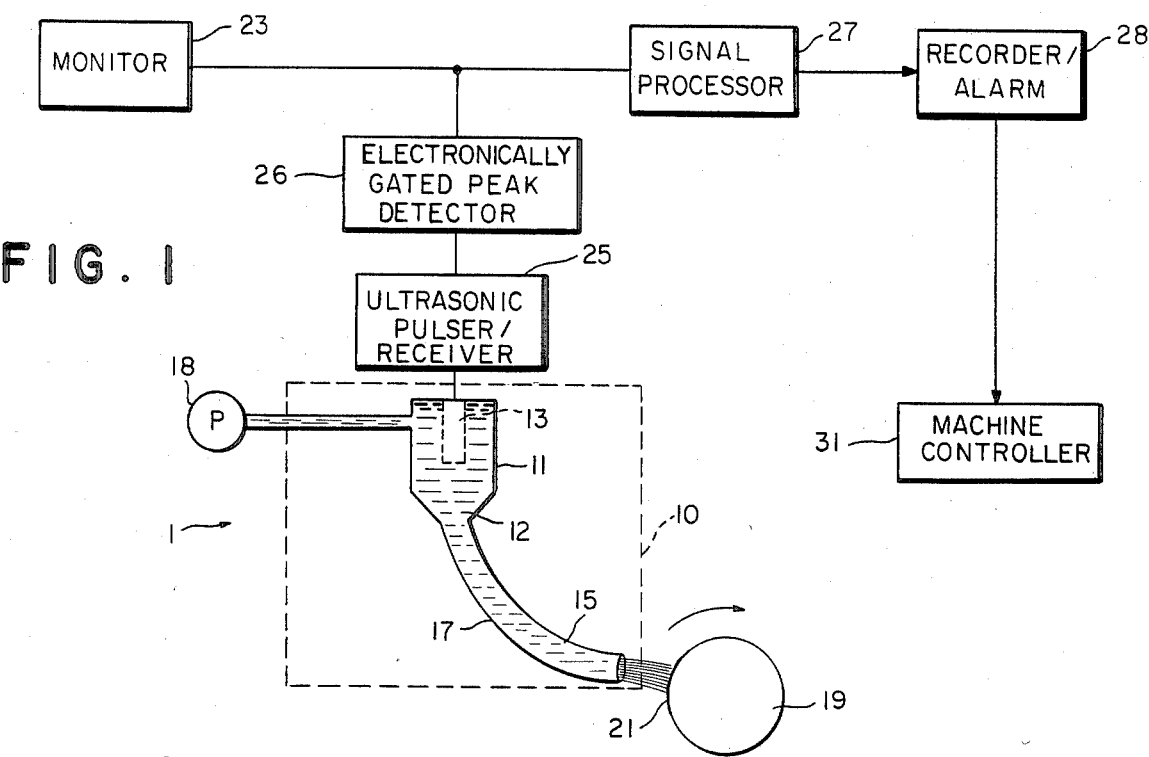
FIG. 1 is a schematic drawing of one embodiment of an ultrasonic real-time system for monitoring part surface topography and tool condition in situ according to the present invention.

Referring now more particularly to an embodiment of the invention selected for illustration in the drawings, FIG. 1 shows a schematic of an ultrasonic real-time system for monitoring part surface topography and tool condition in situ and is designated generally as 1. A squirter assembly 10 has a nozzle 11 which acts as a chamber to submerge a transducer 13 in a fluid 12. A tubing 17 is provided to carry a flowing fluid stream 15 between the nozzle 11 and part 19. Stream 15 in turn acts as a pathway for the transmitted ultrasound to propagate from the transducer 13 to the part surface 21 and for the reflected ultrasound to propagate back to the transducer 13. In actuality, the receiving transducer may be a second adjacently located transducer designed for optimum signal detectability.

For purposes of description, stream 15 will be assumed to be in laminar or non-turbulent flow. However, stream 15 may also be turbulent for some applications. For example, if tubing 17 defines an arcuate path, laminar flow improves the signal carried in the stream 15. However, if the exit end of tube 17 is close to the part surface 21 (e.g. 1 cm.), even a turbulent flow will work. Alternatively, turbulent flow is also satisfactory when tubing 17 defines a straight path and the ultra sound transmitted has a cross-sectional area less than the cross-sectional area of tubing 17.

A liquid pump 18 acts to feed the liquid 12 to the nozzle 11 in sufficient quantity for a laminar flow through the nozzle 11 to the part surface 21 as part 19 rotates or translates. Of course the system may also be used to effectively measure surface roughness of a stationary part. The interior design of the nozzle 11 and its effect on fluid flow is per se known in the prior art as reflected by the aforementioned U.S. patents. An example of a suitable type of nozzle is Model No. WS-100 manufactured by Testech, Inc., Exton, Pa. A monitor 23, typically a CRT screen or oscilloscope, is used to monitor the signal received by the transducer 13 having sensed the wave scattered and reflected from part surface 21. An electronic pulser/receiver 25 sends electric energy pulses to transducer 13 for conversion into ultrasonic wave pulses and to amplify the received signal. An electronically gated peak detector 26 gates out all but the desired received signal. The pulser/receiver 25 and gated peak detector 26 may be obtained from MertoTek, Richland, Wash. as Model MP 215, MR 10 and MD 702. A signal processor 27 processes amplitude information about the desired received signal for subsequent analysis and output to a recorder/alarm device 28. The recorder/alarm 28 may simply record an indication of the amplitude of the received pulses or an average amplitude of the received pulses as calculated by the signal processor 27. The recorder/alarm 28 may also provide an audible or visual alarm whenever the processed amplitude signal indicates excessive tool wear. The output of the processor 27 may additionally or alternatively serve as a feedback control signal for a machine controller 31.

Figure 2:
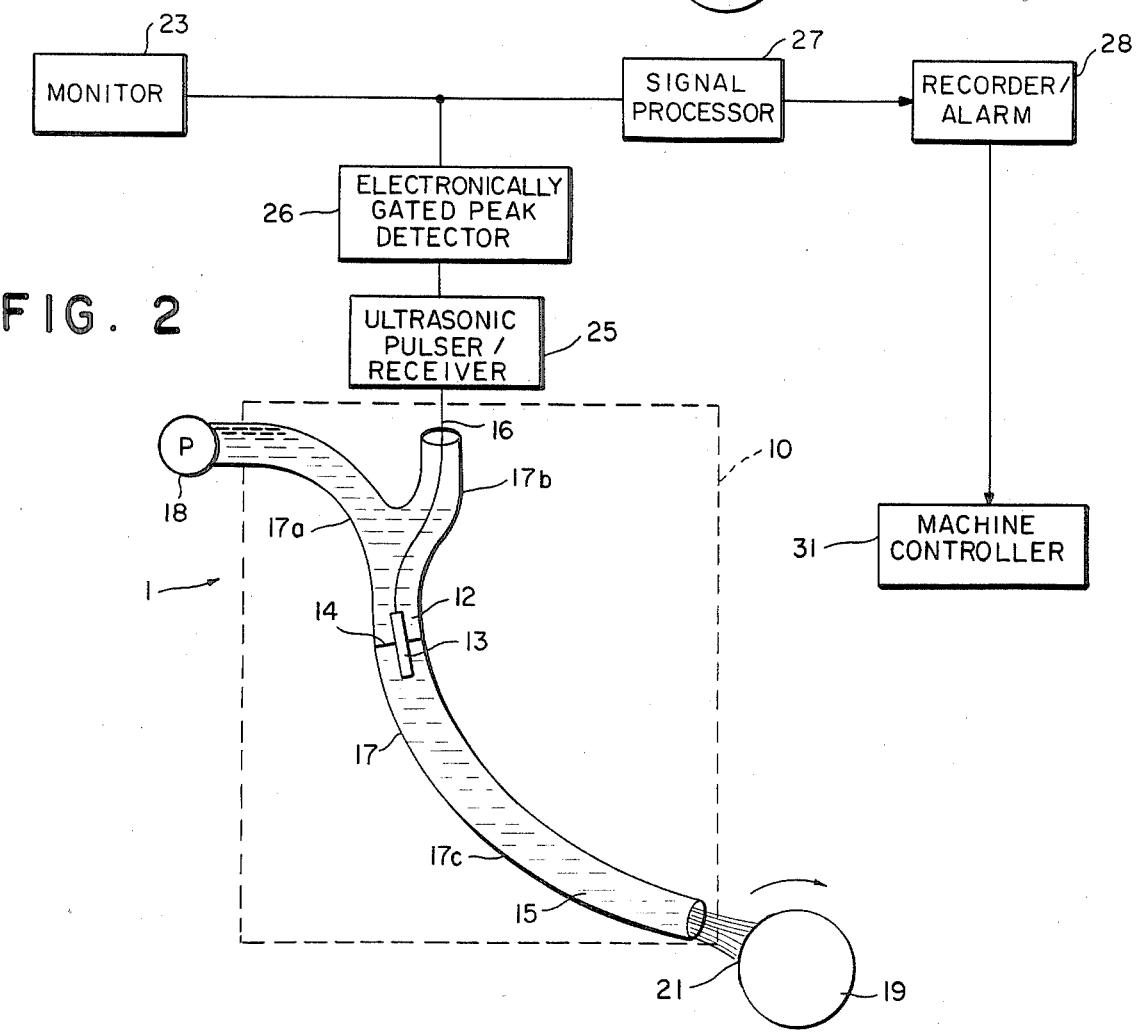
FIG. 2 is a schematic drawing of another embodiment according to the present invention.

FIG. 2 shows a second embodiment of the present invention in which nozzle 11 is removed and replaced by Y-tube 17 having branches 17a, 17b and 17c. Pump 18 feeds liquid 12 through branch 17a. Cable 16 connects transducer 13 to pulser/receiver 25. Transducer 13 is small enough to fit within tube 17 and still allow fluid 12 to flow around it. Transducer 13 is positioned within the tube 17 by means of a spacer 14. An example of such a transducer is the MATEC "pinducer" manufactured by Valpey-Fisher Corp., Hopkinton, Mass. FIG. 3 shows a third embodiment of the present invention in which a single tube 17 is used.

A significant feature shown in FIGS. 1-3 is the tube 17 that acts to guide the ultrasonic waves in a path defined by the curvature of the tube 17. It has been found that the ultrasound energy is surprisingly sufficient even when constrained to follow an arcuate path, such as a U-shape, defined by the curvature of tube 17. Thus, the tube 17 may be flexed to define a curved path for those situations where it may not be practical for nozzle 11 to be near the part surface 21. Natuurally, the tube 17 may also be used to define a straight path where curvature is not needed. In such a case, the straight path may be horizontal without concern for the effects of gravity which were detrimental to non-tubed prior art devices. Comparison tests of various tubing materials capable of holding their own shape, including copper, have shown that polyethylene, polypropolene or nylon tubing, typically of uniform diameter, work well for this application. However, tubing 17 need not be of uniform diameter. Tubing 17 may be tapered to serve as an extension of the taper within nozzle 11. The length of tube 17 is dependent upon the ultrasonic frequency transmitted. For example, at a frequency of 5 megahertz, a 12 inch tube can detect differences in finishes of less than 100 microinches. The length of tube 17 may be greater or less depending on the frequency and application.

The correct flow rate for laminar flow through nozzle 11 and tube 17 while minimizing surface turbulence depends on tube diameter and part size and rotation rate of the part being machined. Typical laminar flow rates are in the range of approximately 1-4 qts/min. Surface speeds up to 1000 ft/min have been successfully tested. Fluid 12 may be water or a water-based cutting oil or coolant liquid commonly used in machine-shop turning centers. Any of these materials is effective as an ultrasonic coupling fluid in the system 10. The fluid may thus serve both as the lubricating/cooling fluid and the coupling fluid. In limited applications, the fluid 12 may also be air in which case the transducer is placed near the surface of the part and no tube is used. Such an application could find utility in the machining of a rolled mill sheet.

In operation, a trigger signal from the pulser 25 starts the horizontal scope sweep of monitor 23. As shown graphically in FIG. 4, after a variable gate delay time $t_v$, electronically gated peak detector 26 opens for a gate width $t_g$ to allow front surface echo signals 50 through the gate for subsequent processing and evaluation while the transmitting pulse 52 and back surface echo signals 54 are gated out from subsequent processing.

A front surface echo 50 is passed onto signal processor 27 as shown in greater detail in FIG. 5. Echo signal 50 is converted from an analog to digital representation by A/D converter 60 for subsequent processing by microprocessor 62. The microprocessor may be programmed to sample and store a plurality of digital echo signal values over a given period of time and take an average value thereof for output as the processed signal 64. By way of example, at a 1 KHz pulse frequency, the microprocessor may sample 100 pulses in 0.1 seconds. Statistical analysis may also be employed as, for example, the calculation of the standard deviation and rejection of any echo pulses outside some number of standard deviations. Alternately, rejection of echo pulses above or below set threshold values may be employed. The ratio of the standard deviation over the average amplitude value may also be utilized as a processing criterion. Whatever processing criterion is utilized, the output thereof is indicated by the processed signal 64.

The processed signal 64 may then be fed to a recorder/alarm 28 and/or machine controller 31. Alarm 66 may be triggered, for example, if the average amplitude of the echo signals falls below a pre-set minimum value. Most easily, the microprocessor 62 will only generate the processed signal 64 if the processing criterion is met. However, the recorder/alarm 28 may itself have some logic selection capability such as to respond to only average value processed signals 64 below a set threshold. Alternatively or additionally, processed signal 64 may be fed to machine controller 31 (as indicated by the dotted line connection in FIG. 5) and trigger machine control operations such as automatically changing a tool bit 70 positioned adjacent a workpiece 72 or shutting down the machine. Further, processed signal 64 may be continually recorded on a recorder 68 for subsequent evaluation of, for example, tool life. An example of such a recorder/alarm 28 is a model number MA 601 manufactured by Metro Tek, Richland, Wash.

As opposed to simply measuring the amplitude of the echo pulse, one may also measure the spectral content of the echo pulse to gain further information on the part surface. This spectral information corresponds to the energy distribution of the echo pulse as a function of frequency.

The advantages of the present invention are numerous. It provides the capability to maintain a constant check on the condition of the cutting tool in an automated machine tool so that the tool can be changed when the cutting edges become damaged or too worn to produce acceptable parts. Even more importantly, the technique works on curved moving surfaces such as would be normally found in an automated turning center.

In the above description, application of the ultrasonic technique has focused on monitoring part surface conditions by measuring the amplitude as a function of frequency of the reflected and scattered ultrasound. Additionally, the same arrangement may be used to determine part dimensions by monitoring ultrasonic wave travel times, i.e., the time it takes for the ultrasonic wave to travel to the part surface and/or the time it takes to travel through the part. Knowledge of the material sound velocity would then permit dimensional calculations from the measured transit times calculated from reflections of the front and back surfaces of the part to be measured. The time of flight measurements may be done in situ and in real time during actual part fabrication.

Thus, although the invention has been described relative to specific embodiments thereof, it is not so limited and numerous variations and modifications thereof would be readily apparent to those skilled in the art in light of the above teaching. It is therefore understood that within the scope of the appended claims, the invention may be practiced otherwise than as specifically described.

What is claimed is:

1. A real-time ultrasonic device for monitoring surface topography of the surface of a part comprising:
   a squirter assembly for transporting a fluid along a curved path to the part surface; and
   a transducer mounted in said squirter assembly and remotely located with respect to the part surface wherein ultrasonic wave pulses generated by said transducer are transmitted to and reflected from the part surface through the fluid along said curved path.

2. A real-time ultrasonic device as claimed in claim 1, wherein said squirter assembly comprises:
   a nozzle; and
   a tube attached to said nozzle.

3. A real-time ultrasonic device as claimed in claim 2, wherein said tube is of uniform diameter.

4. A real-time ultrasonic device as claimed in claim 2, wherein said tube is of tapered diameter.

5. A real-time ultrasonic device as claimed in claim 1, wherein said squirter assembly comprises a tube.

6. A real-time ultrasonic device as claimed in claim 5, wherein said tube is of uniform diameter.

7. A real-time ultrasonic device as claimed in claim 5, wherein said tube is of tapered diameter.

8. A real-time ultrasonic device as claimed in claim 1, wherein the fluid is in laminar flow.

9. A real-time ultrasonic device as claimed in claim 1, further including gate means, connected to said transducer for processing only those ultrasonic waves reflected from said part surface.

10. A real-time ultrasonic device as claimed in claim 1, wherein said part is a machine part and said fluid comprises one of a cooling fluid and a cutting oil.

11. A real-time ultrasonic device as recited in claim 1, wherein said part is moving.

12. A real-time ultrasonic device as recited in claim 11, wherein said moving part is revolving at speeds on the order of 1000 feet per minute.

13. An ultrasonic device for monitoring surface topology of a surface of a part comprising:
   (a) means for transmitting and receiving ultrasonic energy;
   (b) a fluid chamber for containing a fluid, said transmitting and receiving means coupled to said fluid chamber for transmitting ultrasonic energy to fluid in said chamber and for receiving ultrasonic energy from fluid within said chamber; and
   (c) a conduit connected to said fluid chamber and in fluid communication therewith for receiving fluid flowing from said chamber, said conduit extending to a region adjacent said part surface;
   wherein fluid and ultrasonic energy may be directed along a path defined by said conduit.

14. An ultrasonic device as recited in claim 13 further comprising pump means for pumping said fluid in laminar flow through said fluid chamber and subsequently through said conduit.

15. An ultrasonic device as recited in claim 13, wherein said part is moving.

16. An ultrasonic device as recited in claim 15, wherein said moving part is revolving at speeds on the order of 1000 feet per minute.

17. An ultrasonic device as recited in claim 13, wherein said part is a machine part and said fluid comprises one of a cooling fluid and a cutting oil.

18. A method of monitoring a surface of an element comprising the steps of:
   (a) directing a fluid to flow within a conduit,
   (b) flexing said conduit to define a curved path for said flowing fluid,
   (c) generating ultrasonic energy pulses,
   (d) coupling said ultrasonic energy pulses to said flowing fluid,
   (e) directing said flowing fluid to said surface of said element,
   (f) receiving reflected ultrasonic energy pulses along the same curved path as defined in step (b), and
   (g) determining a characteristic of said reflected ultrasonic energy pulses for monitoring said surface.

19. The method as recited in claim 18 further comprising the step of pumping said fluid through said conduit to cause laminar flow therein.

20. The method as recited in claim 18 further comprising the step of moving the element while simultaneously performing at least steps (c), (d), (e), and (f).

21. A real-time ultrasonic system for monitoring a surface of a part to determine part surface topography in situ comprising:
   means for directing a fluid along a path toward a part;
   means for transmitting ultrasonic pulses along said path within said fluid toward the part;
   means for receiving a group of reflected waves from the part for each transmitted pulse;
   means connected to said receiving means for distinguishing one reflected wave of said group of reflected waves as a surface reflection;
   means for processing said surface reflection to generate a processed signal; and
   means connected to said processing means and responsive to said processed signal for providing an indication of part surface topography in situ.

22. A real-time ultrasonic system according to claim 21, wherein the part is moving.

23. A real-time ultrasonic system as claimed in claim 22, wherein the fluid is in laminar flow.

24. A real-time ultrasonic system as claimed in claim 22, wherein the fluid comprises a cutting machine coolant fluid.

25. A real-time ultrasonic system as claimed in claim 22, wherein said path is curved.

26. A real-time ultrasonic system as claimed in claim 22, wherein said transmitting means and said receiving means are a single transducer.

27. A real-time ultrasonic system as claimed in claim 22, wherein said fluid directing means comprises a tube and said transmitting and receiving means comprises a transducer mounted within said tube.

28. A real-time ultrasonic system as claimed in claim 22, wherein said transmitting means and said receiving means comprise multiple transducers.

29. A real-time ultrasonic system as recited in claim 22, wherein said part is a machine part and said fluid comprises one of a cooling fluid and a cutting oil.

30. A real-time ultrasonic system as recited in claim 21, wherein said part is a machine part and said fluid comprises one of a cooling fluid and a cutting oil.

* * * * *